United States Patent [19]
Walker

[11] 4,039,654
[45] Aug. 2, 1977

[54] PROSTANOIC ACID DERIVATIVES

[75] Inventor: Edward Raymond Halstead Walker, Macclesfield, England

[73] Assignee: Imperial Chemical Industries Limited, London, England

[21] Appl. No.: 598,168

[22] Filed: July 22, 1975

[30] Foreign Application Priority Data

Aug. 8, 1974  United Kingdom ............... 34995/74

[51] Int. Cl.$^2$ ............................................ C07C 177/00
[52] U.S. Cl. ............................... 424/305; 260/468 D; 260/468 H; 260/511 D; 542/429; 542/430; 424/317
[58] Field of Search ...................... 260/468 D, 514 D; 424/305, 317

[56] References Cited

U.S. PATENT DOCUMENTS 3,978,229   8/1976   Matsumoto et al. ................. 424/317

FOREIGN PATENT DOCUMENTS 157,344   12/1975   Japan .................................... 260/468

OTHER PUBLICATIONS

Research in Prostaglandins, 2, No. 4, 1973.

*Primary Examiner*—Robert Gerstl
*Attorney, Agent, or Firm*—Cushman, Darby & Cushman

[57] ABSTRACT

This disclosure relates to 16,16-ethylene derivatives of prostaglandin $E_2$ and homologues thereof, which are useful for inhibiting gastric acid production in warm-blooded animals, to processes for their manufacture and pharmaceutical and veterinary compositions containing them, and to a method of inhibiting gastric acid production in warm-blooded animals.

6 Claims, No Drawings

PROSTANOIC ACID DERIVATIVES

This invention relates to novel prostanoic acid derivatives, and in particular it relates to novel prostanoic acid derivatives which inhibit the production of gastric acid in worm blooded animals.

According to the invention, there is provided a prostanoic acid derivative of the formula:

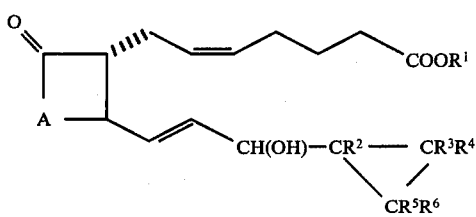

wherein $R^1$ is a hydrogen atom or an alkyl radical of 1 to 10 carbon atoms, $R^2$ is an alkyl radical of up to 10 carbon atoms, $R^3$, $R^4$, $R^5$ and $R^6$, which may be the same or different, are each a hydrogen atom or an alkyl radical of 1 to 4 carbon atoms, and A is a cis-vinylene radical, or an α-hydroxy-ethylene

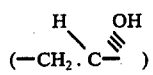

radical, of which the methylene group is bonded to the carbon atom of the ring ketone group, and for those compounds wherein $R^1$ is a hydrogen atom, the pharmaceutically or veterinarily acceptable base addition salts thereof.

A suitable value for $R^1$ when it is an alkyl radical is, for example, a methyl, ethyl, propyl, butyl, hexyl or decyl radical, more particularly such a radical of up to 6 carbon atoms.

A suitable value for $R^2$ is, for example, a methyl, ethyl, propyl, butyl, hexyl, octyl or decyl radical, more particularly such a radical of 2 to 7 carbon atoms.

A suitable value for $R^3$, $R^4$, $R^5$ or $R^6$ when any one or more is an alkyl radical is, for example, a methyl, ethyl, propyl or butyl, especially a methyl radical.

A suitable pharmaceutically or veterinarily acceptable base addition salt is, for example, an ammonium, alkylammonium containing 1 to 4 alkyl radicals each of 1 to 6 carbon atoms, alkanolammonium containing 1 to 3 2-hydroxyethyl radicals, or alkali metal salt, for example and ammonium, triethylammonium, ethanolammonium, diethanolammonium, sodium or potassium salt.

It will be observed that the compounds of the formula I contain at least three asymmetric carbon atoms, namely the two carbon atoms at which the side chains are attached to the ring, (the relative stereochemistry of which is fixed), and the carbon atom of the -CH(OH)- group in the lower side chain. Further asymmetry is introduced in those compounds wherein A is an α-hydroxy-ethylene radical, and in those compounds wherein any one or more of $R^3$, $R^4$, $R^5$ and $R^6$ is an alkyl radical (apart from those compounds wherein $R^3$, $R^4$, $R^5$ and $R^6$ are all the same). It is clear, therefore, that the compounds of the invention can exist as racemates or as a number of optically active forms, and it is to be understood that the invention relates to a racemate, comprising a compound of the formula I and its mirror image, and to any optically active which possesses the gastric acid-inhibiting properties shown by the racemate, it being a matter of common general knowledge how the optical forms may be obtained, and their gastric acid-inhibiting properties determined.

A preferred group of prostanoic acid derivatives of the invention comprises those compounds wherein A is an α-hydroxy-ethylene radical, $R^2$ is an alkyl radical of 2 to 7 carbon atoms, and $R^3$, $R^4$, $R^5$ and $R^6$ are each a hydrogen atom.

Particular prostanoic acid derivatives of the invention are 16,16-ethylene-11α,15-dihydroxy-9-oxo-5-cis,13-trans-prostadienoic acid, 16,16-ethylene-11α,15-dihydroxy-9-oxo-19,20-di-nor-5cis,13-trans-prostadienoic acid and 20-ethylene-11α,15-dihydroxy-9-oxo-5-cis,13-trans-prostadienoic acid.

The novel prostanoic acid derivatives of the invention may be manufactured by methods known in themselves for the manufacture of chemically analogous compounds. Thus, as a further feature of the invention, there is provided a process for the manufacture of a prostanoic acid derivative of the formula I which comprises:

a. the removal, at a pH of between 4 and 7, of a hydroxy-protecting radical from a compound of the formula:

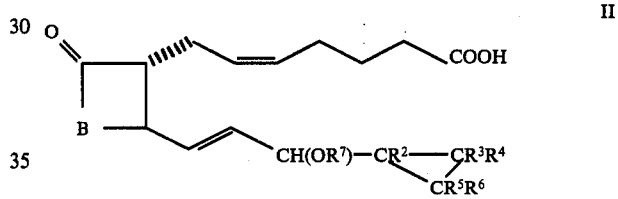

wherein $R^2$, $R^3$, $R^4$, $R^5$ and $R^6$ have the meanings stated above, B is a cis-vinylene radical or a radical of the formula

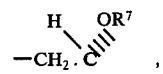

and $R^7$ is a hydroxy-protecting radical capable of being removed at a pH of between 4 and 7, for example a (1-alkoxy-1-alkyl)alkyl radical of 4 to 10 carbon atoms, such as a 1-methoxy-1-methylethyl radical, which may be removed with acid, for example buffered citric acid, at pH 4, a 2-thianyl radical which may be removed, for example, by reaction with a silver salt at neutral pH, or a 3-bromopyran-2-yl radical which may be removed, for example, by reaction with zinc in ethanol, whereafter when a compound wherein $R^1$ is an alkyl radical is required, the product so obtained wherein $R^1$ is a hydrogen atom is esterified by conventional means, for example by reaction with a diazoalkane, or by reaction of a salt thereof, such as the sodium or silver salt, with an alkyl halide, such as an alkyl bromide or alkyl iodide; or b. for those compounds wherein A is a cis-vinylene radical, the dehydration of the corresponding compound wherein A is an α-hydroxy-ethylene radical, for example with a substituted carbodi-imide in the presence of a copper salt as a catalyst, for example N,N'-dicyclohexylcarbodi-imide in the presence of cupric chloride.

A starting material of the formula II, which is used in the process of the invention, may be obtained as follows:

α-butylacrylic acid (III) is reacted with an excess of diazomethane, via pyrolysis of the initially formed pyrazoline, to give methyl 1-butylcyclopropane-carboxylate IV, which is converted by reaction with dimethyl methylphosphonate in the presence of a strong base to the phosphonate V. The phosphonate V is reacted with an aldehyde, for example IV, to give an enone VII, which is reduced with aluminium tri-isopropoxide or di-isobornyloxy aluminium isopropoxide to an enol VIII. The protecting 4-phenylbenzoyl group is hydrolysed to give the diol IX, the hydroxy groups of the diol IX are protected, for example as 1-methoxy-1-methylethoxy radicals by reaction with 2methoxypropene to give X, and the lactone is reduced to a lactol XI by di-isobutyl aluminium hydride. The lactol XI is treated with a (4-carboxybutyl)triphenylphosphonium salt, for example the bromide, in the presence of a strong base, to give the acid XII, which is oxidised, for example with Collin's reagent, (chromium trioxide in methylene dichloride containing two equivalents of pyridine), to give a starting material of the formula II wherein $R^2$ is a butyl radical, $R^3$, $R^4$, $R^5$ and $R^6$ are each a hydrogen atom, B is a radical of the formula

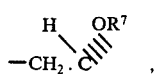

and $R^7$ is a 1-methoxy-1-methylethyl radical.

 III

 IV

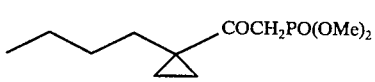 V

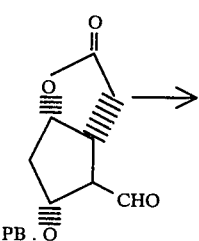 VI

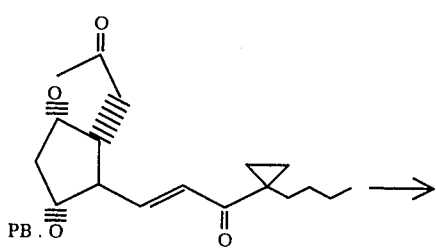 VII

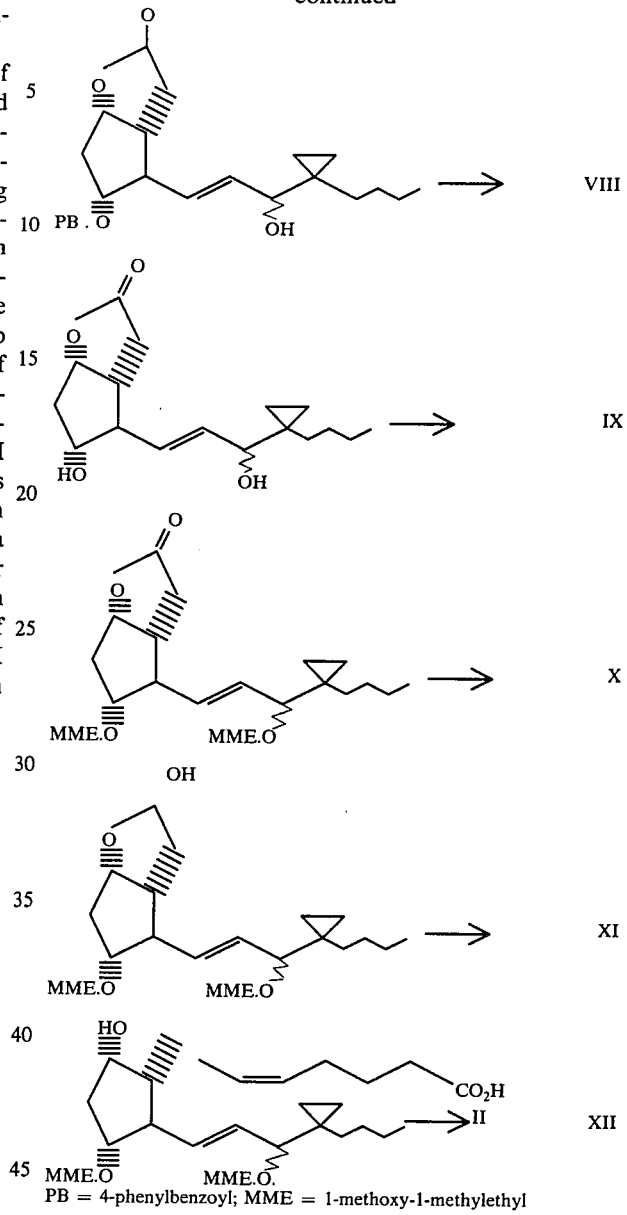

PB = 4-phenylbenzoyl; MME = 1-methoxy-1-methylethyl

Similar starting materials wherein $R^2$, $R^3$, $R^4$, $R^5$ and $R^6$ have others of the above-defined meanings may be obtained by the same general process, using the appropriate analogous, substituted esters IV as the starting point, and similar starting materials wherein A is a cis-vinylene radical may be obtained by the same general process, but using the corresponding known αβ-unsaturated aldehyde in place of the aldehyde VI, and omitting, of course, the reaction for hydrolysing the 4-phenylbenzoyl protecting group (the reaction VIII → IX in the above scheme).

It is, of course, to be understood that an optically active compound of the invention may be obtained either by resolution of racemic compound of the invention with an optically active organic base, or by carrying out the above-described reaction sequence starting from a known optically active aldehyde of the formula VI.

As stated above, the compounds of the invention inhibit the production of gastric acid in warm blooded animals, and in particular they are more effective for this purpose than the previously described, corresponding compounds lacking the 16,16-ethylene group. Thus, for example, 16,16-ethylene-11α,15α-dihydroxy-9-oxo-5-cis, 13-trans-prostadienoic acid reduces gastric acid production by approximately 50–60% when dosed at 1.0 μg./kg./min. and by approximately 65–95% when dosed at 2.0 μg./kg./min. is a standard test in the dog, wherein the stomach contents are sampled via either a Heidenhain pouch or a gastric fistula, and the acid content is determined by titration in conventional manner. In the same test, the corresponding compound lacking the 16,16-ethylene group produces no significant reduction in gastric acid produced. No toxic effects have been noted in test animals at does which produce satisfactory reductions in gastric acid production.

When a prostanoic acid derivative of the invention is to be used for reducing gastric acid production in man, it is to be used in substantially the same way as it is known to use prostaglandin $E_2$ or (15S)- or (15R)-15-methyl-prostaglandin $E_2$ methyl ester for similar purposes. Such prostaglandin analogues have been administered orally, in aqueous solution, at doses of 2.5 to 4.0 mg. for prostaglandin $E_2$, and 100 to 200 μg. for (15S)- and (15R)-15-methylprostaglandin $E_2$ methyl ester. The latter compound has been shown to promote healing of gastric ulcers in Chinese subjects when administered orally as 150 μg. in 20 ml. of water at 6-hourly intervals for 2 weeks.

Thus, according to a further feature of the invention there is provided a pharmaceutical or veterinary composition comprising a prostanoic acid derivative of the formula I as defined above, together with a pharmaceutically or veterinarily acceptable diluent or carrier.

The composition is preferably in the form of a tablet or capsule or a substantially aqueous solution, and a preferred composition is a substantially aqueous solution containing 25 to 150 μg./ml., preferably 75 to 125 μg./ml.

The compositions of the invention may be manufactured by conventional means, and may contain conventional pharmaceutical excipients in addition to the active constituent and the diluent or carrier. The compositions may be stabilised, for example by incorporation of dimethylacetamide, in known manner.

The invention is illustrated, but not limited, by the following Examples:

EXAMPLE 1

A solution of crude 16,16-ethylene-11α,15-di-(1-methoxy-1-methylethoxy)-9-oxo-5-cis, 13-trans-prostadienoic acid (339 mg.) in 2 ml. of pH 3 citric acid buffer and 6 ml. of acetone (pH of mixture = 4), was stirred at room temperature for 18 hours. The solvents were evaporated, and the residue was extracted with ethyl acetate (3 × 2 ml.). The extracts were combined and dried, and the solvent was evaporated to give a mixture of the C-15 epimers of 16,16-ethylene-11α,15-dihydroxy-9-oxo-5-cis,13,-trans-prostadienoic acid, together with 16,16-ethylene-11α-hydroxy-9,15-dioxo-5-cis, 13-trans-prostadienoic acid (which results from some hydrolysis of the 15-(1-methoxy-1-methylethoxy) radical during the preparation of the starting material). The mixture was separated by thin layer chromatography on 2mm. thick silica gel plates (Merck or Darmstadt), developed twice with 2% acetic acid in ethyl acetate. The dihydroxy product was separated into more polar ($R_F=0.6$) and less polar ($R_F=0.7$) epimers.

The n.m.r. spectrum of the more polar epimer showed the following characteristic peaks (δ values):
4.1, 2H, multiplet, >C$\underline{H}$—O—
5.4, 2H, multiplet, cis-olefinic protons
5.65, 2H, multiplet, trans-olefinic protons
The mass spectrum of the 1,11,15-tris(trimethylsilyl)-9-methoxime derivative of the more polar epimer showed M+= 623.3857 (calculated for $C_{32}H_{61}NO_5Si_3$ = 623.3857), and a characteristic peak at 28 m/e units less, corresponding to loss of the 16,16-ethylene radical.

The crude 16,16-ethylene-11α,15-di-(1-methoxy-1-methylethoxy)-9oxo-5-cis, 13-trans-prostadienoic acid used as starting material may be obtained as follows:

α-Butylacrylic acid (1.5 g.) was stirred for 24 hours at 0° C. in the presence of diazomethane (3 eq.) in ether (500 ml.), and for a further 24 hours at room temperature. Evaporation of the solvent gave the pyrozoline, methyl 1-butyl-1-pyrazoline-3-carboxylate, whose n.m.r. spectrum in deuterochloroform showed the following characteristic bands (δ values):
2.0, multiplet, 2H, >C-C$\underline{H}_2$—CH$_2$N=
3.8, singlet, 3H, —COOC$\underline{H}_3$
4.6, triplet, 2H, >C—C$\underline{H}_2$N=, J= 8.Hz
Pyrolysis of the pyrazoline at 100° C. for 1 hour, followed by vacuum distillation gave methyl 1-butylcyclopropanecarboxylate, a mobile oil (b.p. 98°–104° C. at 38 mm. Hg.), whose n.m.r. spectrum showed the following characteristic bands (δ values):
0.6, multiplet, 2H, cyclopropane protons,
3.65, singlet, 3H, —COOC$\underline{H}_3$
n-Butyl-lithium (13.7 ml. of a 1.46M solution in hexane) was added to a solution of dimethyl methylphosphonate (3.1 g.) in dry tetrahydrofuran (30 ml.) at -70° C. in an atmosphere of argon. After 10 minutes, a solution of methyl 1-butylcyclopropanecarboxylate (3.1 g.) in dry tetrahydrofuran (2.7 ml.) was added dropwise, and the mixture was stirred for 2 hours at -70° C. The cold reaction mixture was poured into rapidly stirred 1N hydrochloric acid (20 ml.), and the mixture was adjusted to pH 4 with 1N hydrochloric acid. The mixture was extracted with diethyl ether (3 × 50 ml.), the combined extracts were washed with saturated brine (2 × 10 ml.) and dried, and the solvent was evaporated to give dimethyl 3,3-ethylene-2-oxoheptylphosphonate. The n.m.r. spectrum in deuteriochloroform showed the following characteristic bands (δ values):

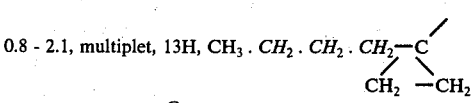

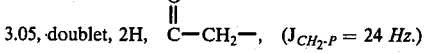

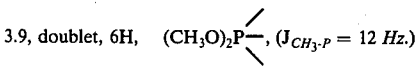

Dimethyl 3,3-ethylene-2-oxoheptylphosphonate (1.89 g.) was suspended in toluene (20 ml.) in an atmosphere of argon, and aqueous 1M sodium hydroxide (6.4 ml.) was added. The two phase mixture was stirred vigorously for 10 minutes, and 4β-formyl-2,3,3aβ,6aβ-tetrahydro-2-oxo-5α-(4-phenylbenzoyloxy)cyclopenteno[b]furan (1.8 g.) was added in toluene (10 ml.). The mixture was stirred vigorously for 1 hour, the layers were allowed to settle and the toluene was separated. The aqueous layer was extracted with ethyl acetate (4 × 10 ml.), the combined organic extracts were washed with brine and dried, and the solvent was evaporated to dryness. Trituration of the residue with ether gave the enone, 4β-[4,4-ethylene-3-oxo-1-trans-octenyl]-2,3,3aβ,6aβ-tetrahydro-5α-(4-phenylbenzoyloxy)-2-oxocyclopenteno[b]furan, $R_F=0.6$ (50% ethyl acetate in toluene). The n.m.r. spectrum in deuteriochloroform showed the following characteristic bands (δ values):

5.15, multiplet, 1H,  
5.35, multiplet, 1H,  } C-5β and C-6αβ protons, 6.35, doublet, 1H, —CH = CH.CO—, )J = 15Hz.), 6.75, doublet doublet, 1H, —CH = CH.CO—, ($J_{1-2}$ = 15Hz.,$J_{1-4}$ = 8 Hz.),
7.5, multiplet, 7H, aromatic protons,
8.1, doublet, 2H, aromatic protons, The enone (1.04 g.) was stirred under an atmosphere of argon at 50° C. with a 0.36M solution of di-isobornyloxyaluminium isopropoxide in toluene (37 ml., 6 equivalents), and after 6 hours, a further quantity of 0.36M di-isobornyl-oxyaluminium isopropoxide (10 ml.) was added. After stirring for 16 hours at room temperature, a final aliquot of the aluminium reagent (10 ml.) was added, and the mixture was stirred at 70° C. for 2 hours. The reaction mixture was cooled, saturated aqueous sodium hydrogen tartrate (40 ml.) was added, and the solution was stirred rapidly at room temperature for 30 minutes. The aqueous layer was separated and extracted and extracted with ethyl acetate (3 × 50 ml.), the combined organic extracts dried, and the solvent was evaporated to give a mixture of isoborneol and the mixed epimers of 4β-[4,4-ethylene-3-hydroxy-1-trans-octenyl]-2,3,3aβ,6aβ-tetrahydro-5α-(4-phenylbenzoyloxy)-2-oxocyclopenteno [b]furan, $R_F$ = 0.3 (50% ethyl acetate in toluene).

The mixture of isoborneol and epimeric unsaturated alcohols produced above was stirred vigorously for 2 hours with finely powdered anhydrous potassium carbonate (334 mg.) in dry methanol (10 ml.). 1N Hydrochloric acid (4.0 ml.) was added, followed by ethyl acetate (100 ml.). The organic layer was separated, washed successively with saturated sodium bircarbonate and saturated brine, dried and evaporated to dryness, and the residue was chromatographed on "Florisil" (trade mark) magnesium silicate (20 g.). Elution with ether removed the by-productss, isoborneol and methyl 4-phenylbenzoate, and subsequent elution with ethyl acetate gave a mixture of the epimeric diols, 4β-[4,4-ethylene-3-hydroxy-1-trans-octenyl]-2,3,3aβ,6aβ-tetrahydro-5α-hydroxy-2-oxocyclopenteno[b]furan, $R_F$ = 0.1 (50% ethyl acetate in toluene), whose n.m.r. spectrum in deuteriochloroform showed the following characteristics bands (δ values):

| 3.8, multiplet, 1H,<br>4.0, multiplet, 1H, | 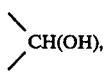 CH(OH), |
|---|---|
| 4.9, multiplet, 1H,<br>5.6, multiplet, 2H, | C-6aβ proton,<br>olefinic protons |

The mixture of epimeric diols (351 mg. ) was dissolved in dry toluene (13 ml.) under an atmosphere of argon, and the solution was cooled to 0° C. Redistilled 2-methoxypropene (1.1 ml.) and anhydrous toluene-p-sulphonic acid in tetrahydrofuran (46 μl. of a 1% solution) were added, and the solution was allowed to warm to room temperature. After 10 minutes, the solution was cooled to 0° C., and after a further 10 minutes, dry pyridine (2 μl.) was added. The solution was then cooled to −70° C., and a 1.95M solution of di-isobutyl aluminium hydride in toluene (1.23 ml.) was added. After 10 minutes at −70° C., methanol (250 μl.) was added, the mixture was allowed to warm to room temperature and was poured into ethyl acetate (25 ml.) and rapidly extracted with 1:1 saturated brine/water (2 × 10 ml.). The organic solution was dried, and the solvent was evaporated to give the mixed epimers of the lactol, 4β-[4,4-ethylene-3-(1-methoxy 1-methylethoxy)-1-transoctenyl]-2,3,3aβ,6aβ-tetrahydro-2-hydroxy-5α-(1-methoxy-1-methylethoxy)-cyclopenteno[b]furan, $R_F$ = 0.2 (50% ethyl acetate in toluene).

(4-carboxybutyl bromide (6.21 g.) and potassium t-butoxide (3.01 g.) were suspended in dry toluene (125 ml.) under an atomosphere of argon, and stirred at 90° C. for 20 minutes to give a deep red 0.108 M toluene solution of the ylide, which was allowed to cool to room temperature. The lactol (530 mg.) was dissolved in dry toluene (20 ml.) under an atmosphere of argon, and the ylide solution was added (33 ml. of the 0.108M toluene solution). After 1 hour at room temperature, water (1 ml.) was added and the toluene evaporated. The residual aqueous solution was extracted with ether (3 × 2 ml.), adjusted to pH 4 with oxalic acid and extracted with a 1:1 mixture of ether and pentane (5 ×2 ml.) to give an acidic extract. The combined acidic extracts were dried, and evaporation of the solvents gave the mixed C-15 epimers of 16,16-ethylene-9α-hydroxy-11α,15-bis-(1-methoxy-1-methylethoxy)- 5-cis, 13-trans-prostadienoic acid, $R_F$ = 0.4 (10% methanol in methylene dichloride).

Dry chromium trioxide (725 mg.) was added to a stirred solution of methylene dichloride (14 ml.) and pyridine (1.17 ml.), and the mixture was stirred at room temperature for 15 minutes. A solution of the mixed C-15 epimers (474 mg.) in methylene dichloride (4 ml.) was added, and the mixture was stirred at room temperature for 15 minutes. Isopropanol (10 drops) was added, and the solution was evaporated to dryness. The residue was washed with ether (4 volumes), the combined ethereal washings were evaporated to dryness, and the pyridine was removed by azeotropic distillation. The residue was then dissolved in ether, the solution was filtered through cotton wool and the solvent was evaporated to give crude 16,16-ethylene-11α,15-bis-(1-methoxy-1-methylethoxy)-9-oxo-5-cis, 13-trans-prostadienoic acid, $R_F$ = 0.5 (10% methanol in methylene chloride), which was used as the required starting material without purification.

EXAMPLE 2

The process described in Example 1 was repeated, using 20-ethyl-16,16-ethylene-11α,15-di-(1-methoxy-1-methyl-ethoxy)-9-oxo-5-cis, 13-trans-prostadienoic acid as the starting material, to give 20-ethyl-16,16-ethylene-11α,15-dihydroxy-9-oxo-5-cis, 13-trans-prostadienoic acid, $R_F$ = 0.7 (thin layer chromatography on silica gel, eluting with 2% acetic acid in ethyl acetate). The n.m.r. spectrum showed the following characteristics peaks (δ values):

4.0, 5H, multiplet, >C$\underline{H}$—O— and —O$\underline{H}$
5.4, 2H, multiplet, cis-olefinic protons
5.7, 2H, multiplet, trans-olefinic protons The mass spectrum of the 1,11,15-tris(trimethylsilyl)-9-methoxime derivative showed M- = 651.4124 (calculated for $C_{34}H_{65}NO_5Si_3$ = 651.4124).

The starting material used in the above process may be obtained by the sequence of processes described in the second part of Example 1, using α-hexylacrylic acid in place of α-butylacrylic acid.

EXAMPLE 3

The process described in Example 1 was repeated, using 16,16-ethylene-11α,15-di-(methoxy-1-methylethoxy)-9-oxo-19,20-dinor-5-cis, 13-trans-prostadienoic acid as the starting material, to give 16,16,-ethylene-11α,15-dihydroxy-9-oxo-19,20-dinor-5-cis,13-trans-prostadienoic acid, $R_F$ = 0.5 (thin layer chromatography on silica gel, eluting with 3% acetic acid in ethyl acetate). The n.m.r. spectrum showed the following characteristics peaks (δ values):

4.2, 5H, multiplet, >C$\underline{H}$-O— and —O$\underline{H}$
5.4, 2H, multiplet, cis-olefinic protons
5.7, 2H, multiplet, trans-olefinic protons The mass spectrum of the 1,11,15-tris(trimethylsilyl)-9-methoxime derivative showed M+ = 595.3510 (calculated for $C_{30}H_{57}NO_5Si_3$ = 595.3545).

The starting material used in the above process may be obtained by the sequence of processes described in the second part of Example 1, using α-ethylacrylic acid in place of α-butylacrylic acid.

EXAMPLE 4

| | |
|---|---|
| 16,16-Ethylene-11α,15-dihydroxy-9-oxo-5-cis,13-trans-prostadienoic acid | 250 μg. |
| Sodium citrate, BP | 30.5 mg. |
| Citric acid, anhydrous, BP | 2.8 mg. |
| Sodium chloride, Ph.Eur. | 35.0 mg. |
| Water for injection, Ph.Eur. | 5.0 ml. |

The sodium citrate, citric acid and sodium chloride are dissolved in most of the water, the prostanoic acid derivative is added, and the solution is made up to volume with the rest of the water, to give an aqueous solution containing 50 μg./ml. of the prostadienoic acid derivative.

The named prostadienoic acid derivative may, of course, be replaced by an equivalent amount of another prostanoic acid derivative of the invention.

What we claim is:
1. A prostanoic acid derivative of the formula:

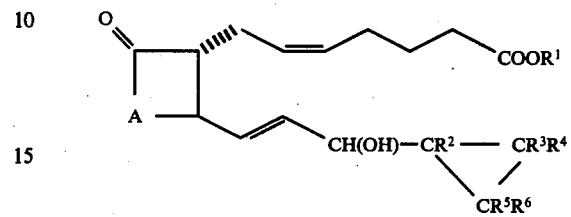

wherein $R^1$ is hydrogen or $C_{1-10}$ alkyl, $R^2$ is $C_{2-7}$ alkyl, $R^3$, $R^5$ and $R^6$ which may be the same or different are each hydrogen or methyl, and A is α-hydroxy-ethylene

of which the methylene is bonded to the carbon of the ring keto group, and, for those compounds wherein $R^1$ is hydrogen, the pharmaceutically or veterinarily acceptable base addition salts thereof.

2. The prostanoic acid derivative of claim 1 wherein $R^1$ is hydrogen or $C_{1-6}$ alkyl, $R^2$ is $C_{2-7}$ alkyl, $R^3$, $R^4$, $R^5$ and $R^6$ which may be the same or different are each hydrogen or methyl.

3. The prostanoic acid derivative of claim 2 wherein $R^3$, $R^4$, $R^5$ and $R^6$ are each hydrogen.

4. The prostanoic acid derivative of claim 3 which is 16,16-ethylene-11α,15-dihydroxy-9-oxo-5-cis, 13-trans-prostadienoic acid, 16,16-ethylene-11α,15-dihydroxy-9-oxo-19,20-di-nor-5-cis, 13-trans-prostadienoic acid or 20-ethyl-16,16-ethylene-11α,15-dihydroxy-9-oxo-5,cis,13-trans-prostadienoic acid.

5. A pharmaceutical or veterinary composition for inhibiting gastric acid secretion consisting of the prostanoic acid derivative of claim 1 together with a pharmaceutically or veterinarily acceptable diluent or carrier.

6. The prostanoic acid derivative of claim 1 which is 16,16-ethylene-11α,15-dihydroxy-9-oxo-5-cis, 13-trans-prostadienic acid.

* * * * *